May 4, 1943. C. B. FOX Plant Pat. 580
PEACH
Filed Jan. 8, 1940
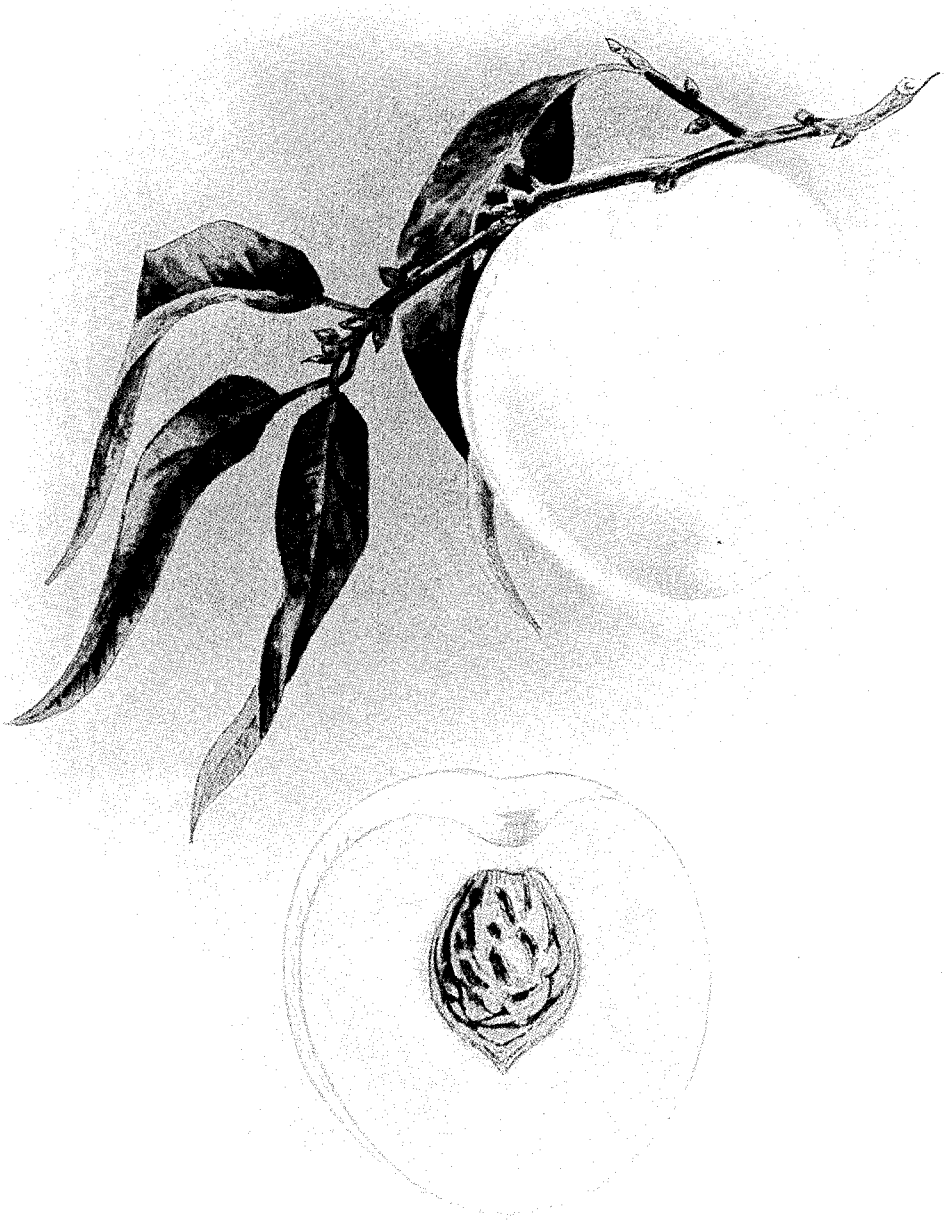
Witness
A. E. Avery
Inventor
Carl Burton Fox
Annubler, Annubler & Davis
Attys.

Patented May 4, 1943

Plant Pat. 580

UNITED STATES PATENT OFFICE

580

PEACH

Carl Burton Fox, Tulsa, Okla.

Application January 3, 1940, Serial No. 312,949

1 Claim. (Cl. 47—62)

The discovery to which this application for patent relates is a peach tree, the parentage of which is not established with certainty other than that the new tree is a seedling offspring from a "J. H. Hale" peach tree. The new tree was first grown from a seed planted in 1930, since which time several thousand other trees of the same variety have been successfully asexually reproduced by grafting.

A standard description of the "J. H. Hale" peach tree with regard to the tree itself; firm texture and juiciness of the flesh of the peach; and general appearance would describe this new variety. It is noticeably and definitely different from the "Hale" peach in that the fruit is larger than the parent (grown in the same climate), has less malic acid, deeper red coloring to the flesh of the peach, a smaller seed and more deeply embedded in the flesh, and less and shorter fuzz. The "J. H. Hale" peach has an average diameter of 3 inches, while this improved peach averages 3½ inches and weighs approximately 11¼ ounces. From the outside skin to the seed, this peach has a superior and improved flavor over the parent peach which has an astringent or bitter tang near the stone, that is common to the "J. H. Hale," Elberta and most freestone peaches. Thus this improved characteristic of this peach entirely eliminates the necessity of cutting away or wasting that part of the fruit adjoining the seed.

The small seed in such a large peach leaves the flashy parts thicker than is usual with peaches and, therefore, gives a greater edible portion. The flesh is tender, fine-grained and firm.

There is a further peculiarity of the fruit that comes into evidence after canning. Thus when the fruit is canned by the regular, accepted cold pack method—notwithstanding 20 minutes cooking at boiling heat in the cans, in a cold pack cooker—even after several months, the canned peach retains a noticeable degree of firmness and has a peculiar flavor suggestive of brandy. So far as known to applicant, all other freestone peaches become soft at an earlier time after canning. In this regard the peaches are improved for commercial use.

The color drawing in duplicate accompanying this application shows a fully matured peach and a cross-section of a peach with the seed.

The color references are to Maerz and Paul's Dictionary of Color.

| Section | Color | Plate | Letter | No. |
|---|---|---|---|---|
| Outside: | | | | |
| Lightest area outside surface. | Aureolin P | 10 | L | 2 |
| shading into | Mellow Glow | 10 | I | 6 |
| Medium shaded area on sun side. | Tangerine | 2 | H | 11 |
| Darkest shaded area on sun side. | Flash | 3 | K | 11 |
| Lightest area of cut cross section. | Light chrome YP. | 10 | L | 4 |
| Inside cross section— | | | | |
| shadinginto medium shaded area. | Carrot R | 10 | C | 11 |
| shading into darkest shaded area. | Carrot R | 3 | G | 11 |
| The inside of the meat takes a slightly lighter color of the sun side ripened section, gradually shading into the lightest (Light chrome YP). | | | | |
| Narrow section close to stone. | Mephisto | 3 | K | 10 |
| Stone: | | | | |
| Lightest section of stone | Chalet R | 6 | K | 10 |
| Darker section and pits of stone. | Garnet+ | 7 | J | 6 |
| Leaves | | 21 | L | 9 |
| Stem | Calla GR | 22 | L | 4 |
| Fruit buds | New Bronze+ | 15 | E | 11 |

As may be seen from the drawing, this peach has a yellow colored skin and meat marked with a deep shade of pink (usually on one side) which extends through the flesh to the seed.

The valuable and novel characteristics of this improved peach reside in the color and the size of the fruit, the thickness of the flesh, the smallness of the seed, and the generation of a brandy flavour when canned. These characteristics are all important commercially and make the variety very desirable from a marketing standpoint. It is a good, all-purpose peach.

I claim:

A new and distinct variety of peach characterized as to novelty by the color and large size of the fruit, thickness, flavor and firmness of the flesh of the fruit which lacks the characteristic bitter tang of the flesh adjacent the stone of the parent plant, the small size of the seed deeply embedded in the flesh, and the excellent eating, shipping and canning qualities of the fruit, and particularly the novel brandy flavor of the fruit when cooked, as described.

CARL BURTON FOX.